United States Patent

Yamada

(10) Patent No.: US 11,304,762 B2
(45) Date of Patent: *Apr. 19, 2022

(54) MAPPING IMAGE DISPLAY CONTROL DEVICE, METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 289 days.

This patent is subject to a terminal disclaimer.

(21) Appl. No.: 15/901,056

(22) Filed: Feb. 21, 2018

(65) Prior Publication Data

US 2018/0243034 A1 Aug. 30, 2018

(30) Foreign Application Priority Data

Feb. 24, 2017 (JP) .............................. JP2017-033711

(51) Int. Cl.
*A61B 34/00* (2016.01)
*A61B 5/08* (2006.01)
(Continued)

(52) U.S. Cl.
CPC .............. *A61B 34/25* (2016.02); *A61B 5/004* (2013.01); *A61B 5/08* (2013.01); *A61B 5/4887* (2013.01);
(Continued)

(58) Field of Classification Search
CPC ....... A61B 34/20; A61B 5/4887; A61B 5/004; A61B 5/08; A61B 34/25; A61B 34/10;
(Continued)

(56) References Cited

U.S. PATENT DOCUMENTS 5,601,582 A * 2/1997 Shelton ............ A61B 17/32056
604/22
8,605,978 B2 * 12/2013 Mizuno ................. G06T 7/0012
382/131

(Continued)

FOREIGN PATENT DOCUMENTS

JP 2015-177523 A 10/2015

OTHER PUBLICATIONS

Tawhai et al. "Chapter 6: Modeling of the Pulmonary Vasculature". Textbook of Pulmonary Vascular Disease, Springer Science+ Business Media, LLC 2011. p. 91-103. (Year: 2011).*

(Continued)

*Primary Examiner* — Oommen Jacob
(74) *Attorney, Agent, or Firm* — Birch, Stewart, Kolasch & Birch, LLP

(57) ABSTRACT

An arrival position information estimation unit that estimates arrival position information at which an extension line of a peripheral branch included in a bronchial region arrives at a surface of a lung region, and estimates assumed mapping information other than the arrival position information of a specific peripheral branch on the basis of a preset condition in a case where the specific peripheral branch is set as a target branch, and a display control unit that generates a mapping image obtained by mapping the arrival position information of the specific peripheral branch and the assumed mapping information to a surface of the lung region and displays the mapping image on a display unit are included.

15 Claims, 11 Drawing Sheets

(51) Int. Cl.

| | | |
|---|---|---|
| *A61B 5/00* | (2006.01) | |
| *A61B 6/00* | (2006.01) | |
| *G06T 7/11* | (2017.01) | |
| *G06T 7/187* | (2017.01) | |
| *G06T 17/00* | (2006.01) | |
| *G06T 19/20* | (2011.01) | |
| *G06T 7/00* | (2017.01) | |
| *A61B 34/10* | (2016.01) | |
| *A61B 34/20* | (2016.01) | |
| *A61B 17/00* | (2006.01) | |
| *A61B 5/05* | (2021.01) | |
| *A61B 6/03* | (2006.01) | |

(52) U.S. Cl.
CPC .............. *A61B 6/466* (2013.01); *A61B 6/481* (2013.01); *A61B 6/50* (2013.01); *A61B 6/5217* (2013.01); *A61B 34/10* (2016.02); *A61B 34/20* (2016.02); *G06T 7/0012* (2013.01); *G06T 7/11* (2017.01); *G06T 7/187* (2017.01); *G06T 17/00* (2013.01); *G06T 19/20* (2013.01); *A61B 5/05* (2013.01); *A61B 6/032* (2013.01); *A61B 6/4405* (2013.01); *A61B 2017/00809* (2013.01); *A61B 2034/104* (2016.02); *A61B 2034/105* (2016.02); *A61B 2034/2057* (2016.02); *A61B 2034/2065* (2016.02); *G06T 2200/04* (2013.01); *G06T 2207/10024* (2013.01); *G06T 2207/10081* (2013.01); *G06T 2207/10088* (2013.01); *G06T 2207/30061* (2013.01); *G06T 2207/30096* (2013.01)

(58) Field of Classification Search
CPC .. A61B 2017/00809; A61B 2034/2057; A61B 2034/105; A61B 6/481; A61B 6/5217; A61B 6/50; A61B 6/466; A61B 6/4405; A61B 5/055; A61B 6/032; A61B 2034/104; A61B 2034/2065; G06T 7/187; G06T 19/20; G06T 7/0012; G06T 7/11; G06T 17/00; G06T 2200/04; G06T 2207/10088; G06T 2207/30061; G06T 2207/10081; G06T 2207/10024; G06T 2207/30096

See application file for complete search history.

(56) References Cited

U.S. PATENT DOCUMENTS

| | | | | |
|---|---|---|---|---|
| 2005/0107679 | A1* | 5/2005 | Geiger | G06T 19/003 600/407 |
| 2006/0056685 | A1* | 3/2006 | Kiraly | G06T 7/0012 382/165 |
| 2007/0167714 | A1* | 7/2007 | Kiraly | A61B 1/0005 600/407 |
| 2009/0054729 | A1* | 2/2009 | Mori | A61B 1/00009 600/114 |
| 2009/0161927 | A1* | 6/2009 | Mori | A61B 6/466 382/128 |
| 2010/0149183 | A1* | 6/2010 | Loewke | G06K 9/32 345/424 |
| 2011/0184238 | A1* | 7/2011 | Higgins | G06T 7/75 600/117 |
| 2011/0243403 | A1* | 10/2011 | Mizuno | G06T 7/0012 382/128 |
| 2011/0311124 | A1* | 12/2011 | Ohnishi | G06T 7/0012 382/134 |
| 2013/0009958 | A1* | 1/2013 | Kitamura | G06T 7/12 345/424 |
| 2013/0303893 | A1* | 11/2013 | Duindam | A61B 5/0044 600/424 |
| 2015/0187118 | A1* | 7/2015 | Masumoto | A61B 6/468 345/419 |
| 2015/0282887 | A1* | 10/2015 | Yamada | G06T 19/003 600/410 |
| 2015/0305650 | A1* | 10/2015 | Hunter | A61B 5/1107 600/424 |

OTHER PUBLICATIONS

Sato et al. "Use of virtual assisted lung mapping (VAL-MAP), a bronchoscopicmultispot dye-marking technique using virtual images, for precisenavigation of thoracoscopic sublobar lung resection". The Journal of Thoracic and Cardiovascular Surgery, vol. 147, No. 6. Jun. 2014. (Year: 2014).*

Sato et al. "Thoracoscopic wedge lung resection using virtual-assisted lung mapping", [online], Jun. 12, 2014, Asian Cardiovascular and Thoracic Annals, <URL: http://aan.sagepub.com/content/early/2014/06/12/0218492314539332>.

* cited by examiner

MAPPING IMAGE DISPLAY CONTROL DEVICE, METHOD, AND PROGRAM

CROSS-REFERENCE TO RELATED APPLICATION

This application claims priority from Japanese Patent Application No. 2017-037061, filed on Feb. 28, 2017, the disclosure of which is incorporated by reference herein in its entirety.

BACKGROUND

Field of the Invention

The present invention relates to a device, method, and program for simulating a position of a lung surface on which a dye is exuded in a case where the dye is sprayed onto a peripheral part of a bronchus, and generating and displaying a mapping image obtained by mapping the position to the lung surface.

Related Art

In recent years, a Virtual Assisted Lung Mapping (VAL-MAP) method has been proposed as a method of marking a resection region of a lung (see Masaaki Sato, and eight others, "Thoracoscopic wedge lung resection using virtual-assisted lung mapping", [online], Jun. 12, 2014, Asian Cardiovascular and Thoracic Annals, <URL: http://aan.sagepub.com/content/early/2014/06/12/0218492314539332>). In this VAL-MAP method, a bronchus located around a tumor is arbitrarily selected, and a procedure of a bronchoscope is performed on the bronchus. A catheter is caused to advance to a peripheral part of the bronchus and a dye is sprayed onto the peripheral part to stain the lung surface.

By staining the lung surface in this manner, it is possible to predict a position of the tumor with high accuracy using the stained region as a landmark at the time of a thoracotomy or a thoracoscopic procedure.

Here, in a case where the VAL-MAP method described above is performed, a stained part of the lung surface may be desired to be confirmed through simulation before surgery in a case where the bronchus is selected and sprayed with a dye. Therefore, a method of simulating a position that can be stained on the lung surface on the basis of a bronchial region extracted by image processing using a three-dimensional image such as a computed tomography (CT) image captured in advance is conceivable.

In a case where such a simulation is performed, since the bronchial region is usually not in contact with the lung surface, extending the bronchial region to the lung surface is conceivable. As a method of extending the bronchial region to the lung surface, for example, a method of extracting a route of the bronchial region as a graph structure and extending a terminal of the graph structure to the lung surface is conceivable (see, for example, JP2015-177523A).

However, according to an examination result of the inventors, even in a case where bronchoscope treatment for staining is performed in consideration of a simulation result after the above-described simulation is performed, it has been found that a position as simulated is not stained in some cases. Therefore, a use as an index for an assumed resection region may be difficult, and in the worst case, it is necessary for the staining treatment to be performed again.

Further, in an actual site, a CT image is captured after staining treatment in order to confirm where staining has been performed. This CT image is analyzed, a deviation between an actual staining position and a position of a simulation result is recognized, and a plan for resection is established. In a case where the deviation can be recognized in advance, it is not necessary to capture the CT image after surgery as described above.

As a result of further investigation, the inventors have discovered two factors as factors of the positional deviation between the actual staining position and the simulation result as described above. One factor is that a bronchus near a peripheral part is deformed in a case where a bronchoscope is inserted.

Further, since a bronchoscope cannot be inserted due to a smaller diameter of the bronchial region nearer to the peripheral part, a catheter is inserted. In this case, an insertion direction of the catheter is determined while observing an X-ray fluoroscopic image captured in real time. However, since a line-of-sight direction of an operator with respect to the X-ray fluoroscopic image is fixed, the catheter is likely to be erroneously inserted into a branch in a depth direction. This erroneous insertion is considered to be another factor.

The prevent invention has been made in view of the above circumstances, and an object of the present invention is to provide a mapping image display control device, method, and program capable of generating and displaying a mapping image in consideration of deformation of a bronchus and an erroneous insertion of a catheter in a case where a position of a lung surface on which a dye is exuded is simulated and the mapping image is displayed in a case where the dye is sprayed onto the peripheral part of a bronchus.

SUMMARY

A mapping image display control device of the present invention comprises: a lung region extraction unit that extracts a lung region included in a three-dimensional image; a bronchial region extraction unit that extracts a bronchial region included in the lung region; a branch position information acquisition unit that acquires information on a branch position of the bronchial region; an arrival position information estimation unit that estimates arrival position information at which an extension line of a peripheral branch included in the bronchial region arrives at a surface of the lung region on the basis of the information on the branch position, and estimates assumed mapping information other than the arrival position information of a specific peripheral branch on the basis of a preset condition in a case where the specific peripheral branch is set as a target branch; and a display control unit that generates a mapping image obtained by mapping the arrival position information of the specific peripheral branch and the assumed mapping information to the surface of the lung region and displays the mapping image on a display unit.

Further, in the mapping image display control device of the present invention, the arrival position information estimation unit may estimate the assumed mapping information on the basis of a condition of deformation of a bronchus in a case where a bronchoscope is inserted into the bronchus.

Further, in the mapping image display control device of the present invention, the arrival position information estimation unit may estimate position information at which an extension line of a peripheral branch different from the specific peripheral branch extending from a branch position present between a proximal end portion of the bronchial region and the specific peripheral branch arrives at a surface of the lung region, as the assumed mapping information.

Further, in the mapping image display control device of the present invention, the arrival position information estimation unit may estimate position information at which an extension line of a peripheral branch different from the specific peripheral branch extending from a first branch position or a second branch position from the terminal of the specific peripheral branch arrives at a surface of the lung region, as the assumed mapping information.

Further, in the mapping image display control device of the present invention, the arrival position information estimation unit may estimate a straight line set on the basis of the information on the branch position and the peripheral branch as an extension line of the branch.

Further, in the mapping image display control device of the present invention, the arrival position information estimation unit may estimate a straight line set on the basis of a terminal of the peripheral branch and information on a first branch position from the terminal as an extension line of the peripheral branch.

Further, in the mapping image display control device of the present invention, the arrival position information estimation unit may perform spline interpolation using a point on the peripheral branch and a point specified on the basis of the information on the first branch position from the terminal of the peripheral branch, and estimate a curve obtained by the spline interpolation as an extension line of the peripheral branch.

Further, in the mapping image display control device of the present invention, the arrival position information estimation unit may specify the peripheral branch on the basis of the information on the branch position, specify a dominant region of the specified peripheral branch in the lung region, and estimate a straight line connecting a center of gravity of the dominant region to a terminal of the peripheral branch as an extension line of the peripheral branch.

Further, in the mapping image display control device of the present invention, the arrival position information estimation unit may specify the peripheral branch on the basis of the information on the branch position, specify a dominant region of the specified peripheral branch in the lung region, and estimate a center of gravity of a region that is a surface of the lung region in a surface of the dominant region as the arrival position information.

Further, the mapping image display control device of the present invention may further comprise a blood vessel region extraction unit that extracts a blood vessel region included in the lung region, and the arrival position information estimation unit may estimate an extension line of the peripheral branch on the basis of information on the blood vessel region and the branch position.

Further, in the mapping image display control device of the present invention, the blood vessel region extraction unit may extract at least one of a pulmonary vein region or a pulmonary artery region as the blood vessel region.

Further, in the mapping image display control device of the present invention, the display control unit may set a region on the basis of the arrival position information of the specific peripheral branch and the assumed mapping information, generate a mapping image obtained by mapping the region on the surface of the lung region, and display the mapping image on the display unit.

A mapping image display control method of the present invention comprises: extracting a lung region included in a three-dimensional image; extracting a bronchial region included in the lung region; acquiring information on a branch position of the bronchial region; estimating arrival position information at which an extension line of a peripheral branch included in the bronchial region arrives at a surface of the lung region on the basis of the information on the branch position, and estimating assumed mapping information other than the arrival position information of the specific peripheral branch on the basis of a preset condition in a case where the specific peripheral branch is set as a target branch; and generating a mapping image obtained by mapping the arrival position information of the specific peripheral branch and the assumed mapping information to the surface of the lung region and displaying the mapping image on a display unit.

A mapping image display control program of the present invention that causes a computer to function as: a lung region extraction unit that extracts a lung region included in a three-dimensional image; a bronchial region extraction unit that extracts a bronchial region included in the lung region; a branch position information acquisition unit that acquires information on a branch position of the bronchial region; an arrival position information estimation unit that estimates arrival position information at which an extension line of a peripheral branch included in the bronchial region arrives at a surface of the lung region on the basis of the information on the branch position, and estimates assumed mapping information other than the arrival position information of a specific peripheral branch on the basis of a preset condition in a case where the specific peripheral branch is set as a target branch; and a display control unit that generates a mapping image obtained by mapping the arrival position information of the specific peripheral branch and the assumed mapping information to the surface of the lung region and displays the mapping image on a display unit.

Another mapping image display control device of the present invention comprises: a memory that stores instructions to be executed by a computer, and a processor configured to execute the stored instructions, and is configured such that the processor executes a process of extracting a lung region included in a three-dimensional image; a process of extracting a bronchial region included in the lung region; a process of acquiring information on a branch position of the bronchial region; a process of estimating arrival position information at which an extension line of a peripheral branch included in the bronchial region arrives at a surface of the lung region on the basis of the information on the branch position, and estimating assumed mapping information other than the arrival position information of the specific peripheral branch on the basis of a preset condition in a case where the specific peripheral branch is set as a target branch; and a process of generating a mapping image obtained by mapping the arrival position information of the specific peripheral branch and the assumed mapping information to the surface of the lung region and displaying the mapping image on a display unit.

According to the mapping image display control device, method, and program of the present invention, the lung region included in the three-dimensional image is extracted, the bronchial region included in the lung region is extracted, information on a branch position of the bronchial region is acquired. The arrival position information at which an extension line of a peripheral branch included in the bronchial region arrives at a surface of the lung region is estimated on the basis of the information on the branch position. The assumed mapping information other than the arrival position information of the specific peripheral branch is estimated on the basis of a preset condition in a case where the specific peripheral branch is set as a target branch, and the mapping image obtained by mapping the arrival position information of the specific peripheral branch and the assumed mapping information to the surface of the lung region is generated and displayed.

That is, since the condition considering, for example, the erroneous insertion of the catheter and the deformation of the bronchus described above is preset, the assumed mapping information is estimated on the basis of the condition and the mapping image is generated and displayed, a user can determine a resection region of a tumor or the like in consideration of a positional deviation in a case where a dye is actually sprayed onto the peripheral part of the bronchus.

Further, since a deviation of a staining position can be recognized in advance, it is not necessary to perform capturing of a CT image for confirming the staining position after staining treatment.

DETAILED DESCRIPTION

Figure 1:
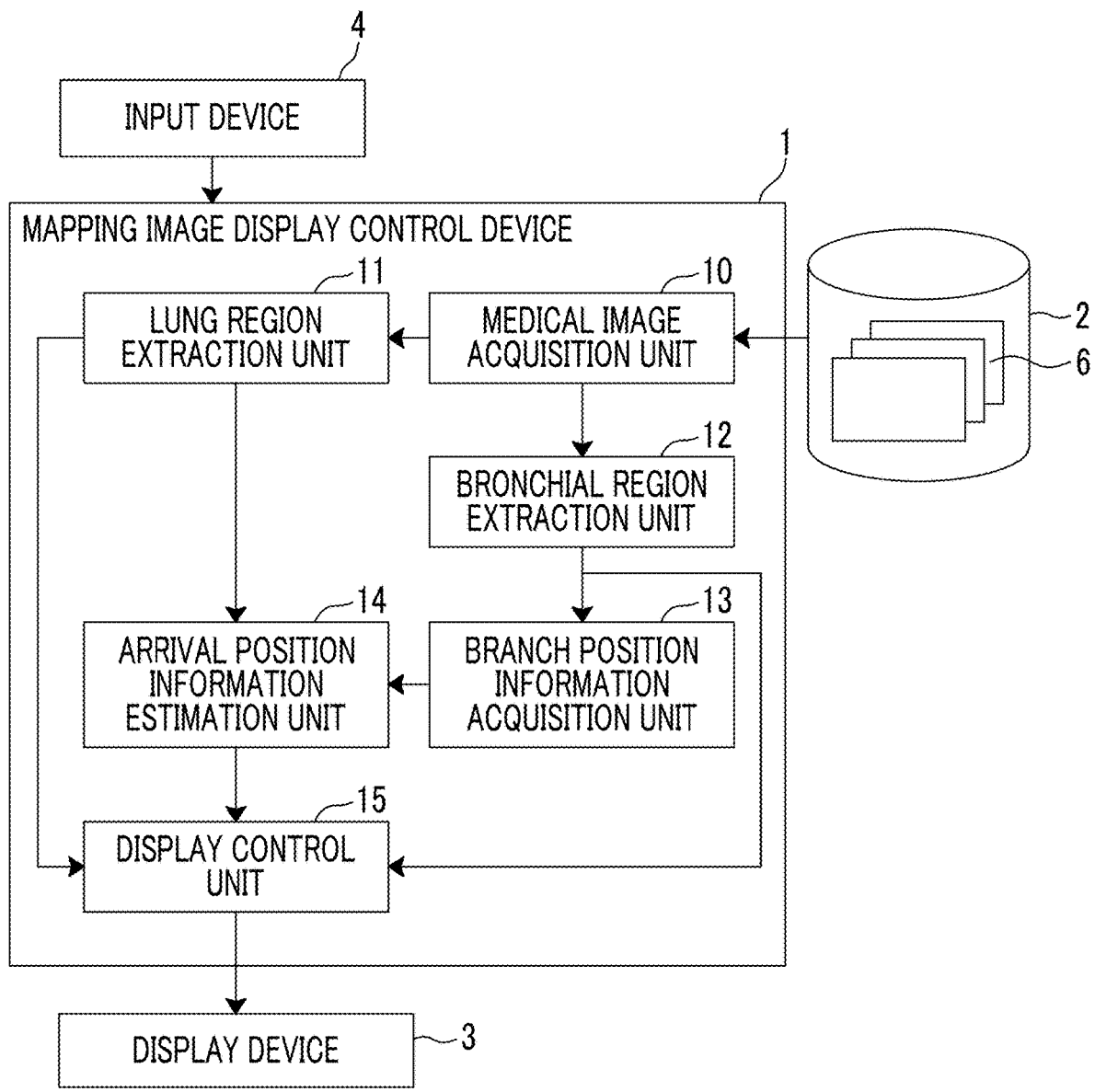
FIG. 1 is a block diagram illustrating a schematic configuration of a medical image diagnosis support system using an embodiment of a mapping image display control device, method, and program of the present invention.

Hereinafter, a medical image diagnosis support system using an embodiment of a mapping image display control device, method, and program of the present invention will be described in detail with reference to the drawings. FIG. 1 is a block diagram illustrating a schematic configuration of a medical image diagnosis support system according to a first embodiment of the present invention.

A medical image diagnosis support system of this embodiment performs support in a case where the VAL-MAP method described above is performed and, basically, simulates a position of a lung surface on which a dye is exuded in a case where the dye is sprayed onto a peripheral part of a bronchus, and generates and displays a mapping image obtained by mapping the position to the lung surface. By observing this mapping image, a doctor can recognize a position of the lung surface at which the dye is exuded in a case where the bronchus is selected and the dye is sprayed onto the peripheral part thereof, and therefore, appropriately select the bronchus that is sprayed with the dye before surgery.

Further, in the medical image diagnosis support system of this embodiment, in a case where a doctor selects a bronchus to which a dye is sprayed and actually inserts a bronchoscope into the selected bronchus as described above, a mapping image is generated and displayed on the assumption that a catheter is erroneously inserted into a different bronchus and a dye is sprayed as described above.

The medical image diagnosis support system of this embodiment specifically includes a mapping image display control device 1, a medical image storage server 2, a display device 3 (corresponding to a display unit), and an input device 4, as illustrated in FIG. 1.

The mapping image display control device 1 is a mapping image display control device in which the mapping image display control program of this embodiment is installed on a computer.

The mapping image display control device 1 includes a central processing unit (CPU), a semiconductor memory, and a storage device such as a hard disk or a solid state drive (SSD). The mapping image display control program of this embodiment is installed on the storage device. By the central processing unit executing the mapping image display control program, a medical image acquisition unit 10, a lung region extraction unit 11, a bronchial region extraction unit 12, a branch position information acquisition unit 13, an arrival position information estimation unit 14, and a display control unit 15 illustrated in FIG. 1 operate.

The mapping image display control program is recorded on a recording medium such as a digital versatile disc (DVD), a compact disc read only memory (CD-ROM), distributed, and installed on the computer from the recording medium. Further, the mapping image display control program is stored in a state in which a storage device of a server computer connected to a network or a network storage can be accessed from the outside, and is downloaded and installed on the computer in response to a request.

The medical image acquisition unit 10 acquires a three-dimensional image 6 of a chest of a patient that has been imaged in advance. The three-dimensional image 6, for example, is obtained by imaging the chest of the patient using a computed tomography (CT) device, a magnetic resonance imaging (MRI) device, or the like.

The three-dimensional image 6 is stored in advance in the medical image storage server 2 together with patient identification information, and the medical image acquisition unit 10 reads out the three-dimensional image 6 having the identification information from the medical image storage server 2 on the basis of the patient identification information input by the user using the input device 4 or the like, and temporarily stores the three-dimensional image 6.

The lung region extraction unit 11 performs a process of extracting a lung region from the three-dimensional image 6 of the chest acquired by the medical image acquisition unit 10. A known scheme such as a method of extracting the lung region by histogramming a signal value at each pixel position of the three-dimensional image 6 since a lung field is a region in which there is air, and performing threshold process on the lung region or a region spreading method based on a seed point indicating a lung region can be used as a method of extracting the lung region.

The bronchial region extraction unit 12 performs a process of extracting a bronchial region included in the lung region of the three-dimensional image 6 of the chest. A bronchus included in the three-dimensional image 6 is indicated as a region indicating a small pixel value because a pixel inside the bronchus corresponds to an air region, but a bronchial wall is considered to be a cylinder or linear structure indicating a relatively large pixel value. Therefore, structure analysis of a shape based on a distribution of pixel values is performed for each pixel to extract the bronchus. For example, as in the method described in JP2012-200403A, it is possible to extract the bronchial region and a graph structure in which the bronchial region is thinned by performing Hessian analysis on the basis of the pixel value of each pixel. Other known schemes may be used as the method of extracting a bronchial region.

The branch position information acquisition unit 13 acquires information on a branch position of the bronchial region extracted by the bronchial region extraction unit 12. Specifically, the branch position information acquisition unit 13 classifies a graph structure of the bronchial region extracted by the bronchial region extraction unit 12 into a start point, an end point, branch points, and edges, and acquires position information of the branch point as the information on the branch position of the bronchial region.

The arrival position information estimation unit 14 estimates arrival position information at which an extension line of a peripheral branch included in the bronchial region arrives at a surface of the lung region on the basis of the information on the branch position acquired by the branch position information acquisition unit 13.

Here, in the VAL-MAP method, in a case where a dye is sprayed onto a peripheral part of the bronchus, a position at which the dye arrives at a lung surface and is exuded after passing through the inside of a tissue of a lung can be estimated as a position at which an extension line of the peripheral branch of the bronchus arrives at the lung surface.

Therefore, the arrival position information estimation unit 14 extracts the graph structure of the bronchial region from the three-dimensional image, and estimates a straight line set on the basis of information on a terminal of the peripheral branch included in the graph structure and the branch position acquired by the branch position information acquisition unit 13 as an extension line of the peripheral branch of the bronchial region. The arrival position information at which the extension line arrives at the surface of the lung region is estimated as a position at which the dye arrives at the lung surface.

Figure 2:
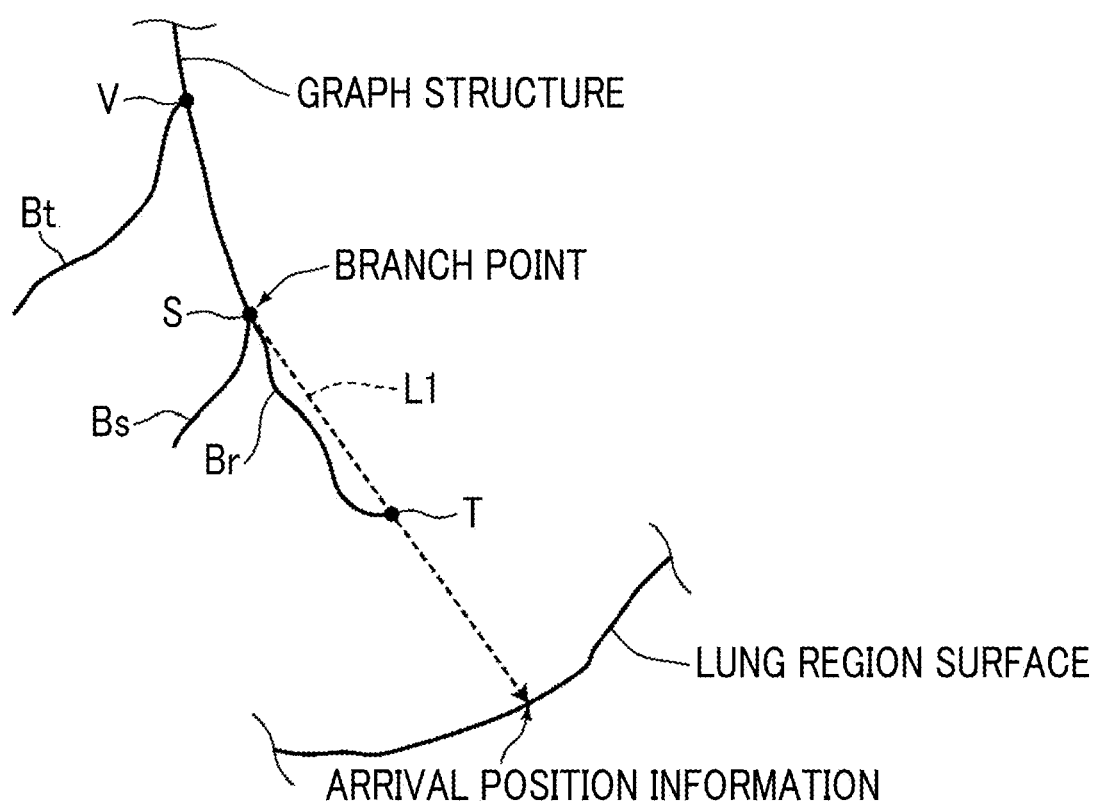
FIG. 2 is a diagram illustrating a method of obtaining arrival position information.

Specifically, as illustrated in FIG. 2, the arrival position information estimation unit 14 estimates a straight line connecting a terminal T of a branch Br of the peripheral part of the graph structure of the bronchial region to a first branch point S from the terminal T as an extension line L1 of the branch Br of the peripheral part. The arrival position information estimation unit 14 acquires an intersection between the extension line L1 and a lung region surface as the arrival position information. The first branch point from the terminal T is a first branch in a direction from the terminal of the bronchial region to a proximal end portion side (upstream side) of the bronchial region.

In this embodiment, the first branch point from the terminal T is used, but the present invention is not limited thereto, and the extension line may be set using a second branch point, a third branch point, or the like from the terminal T.

Further, although the terminal T of the peripheral branch of the graph structure of the bronchial region and the first branch point S from the terminal T are connected in this embodiment, the branch point S may not necessarily be used and a point near the branch point S may be used as long as substantially the same result can be obtained using the point. That is, the straight line set on the basis of the information on the branch position and the terminal of the peripheral branch in the graph structure is assumed to also include a straight line that is set by connecting the terminal T of the peripheral branch and the point near the branch point S.

The arrival position information need not necessarily be coordinates of one point, and a two-dimensional or three-dimensional range including the intersection may be acquired as the arrival position information. The arrival position information is information indicating an arrival point or an arrival range in which the dye arrives at the lung surface after the dye passes through the inside of a tissue of the lung in a case where the dye is sprayed onto the peripheral part of the bronchus.

Further, the arrival position information estimation unit 14 of this embodiment assumes erroneous insertion of the catheter described above in a case where a specific peripheral branch among peripheral branches of the bronchial region is a target branch to which the dye is sprayed, and estimates the arrival position information of the peripheral branch into which the catheter is erroneously inserted as assumed mapping information. Specifically, the arrival position information estimation unit 14 of this embodiment estimates arrival position information of a specific peripheral branch different from a specific peripheral branch extending from the branch position present between a proximal end portion of the bronchial region and the specific peripheral branch described above, as assumed mapping information. As a branch position present between the proximal end portion of the bronchial region and the specific peripheral branch, for example, in a case where a peripheral branch Br illustrated in FIG. 2 is set as the specific peripheral branch, a first branch point S from the terminal T may be used or a second branch point V from the terminal T may be used. In a case where the branch point S is used, arrival position information of a peripheral branch Bs different from the peripheral branch Br is estimated as the assumed mapping information. Further, in a case where the branch point V is used, arrival position information of the peripheral branch Bs and a peripheral branch Bt different from the peripheral branch Br is estimated as the assumed mapping information.

Further, the display control unit 15 generates a volume rendering image of the lung region and the bronchial region on the basis of the lung region extracted by the lung region extraction unit 11 and the bronchial region extracted by the bronchial region extraction unit 12. Opacity of the volume rendering image of the lung region is set to such a degree that the bronchial region within the lung region can be visually recognized, and colors of the lung region and the bronchial region are set to different colors.

Further, the display control unit 15 generates a mapping image obtained by superimposing the arrival position information estimated by the arrival position information estimation unit 14, the assumed mapping information, and the extension line set in a case where the arrival position information is estimated, to the volume rendering image of the lung region and the bronchial region, and displays the mapping image on the display device 3.

Figure 3:
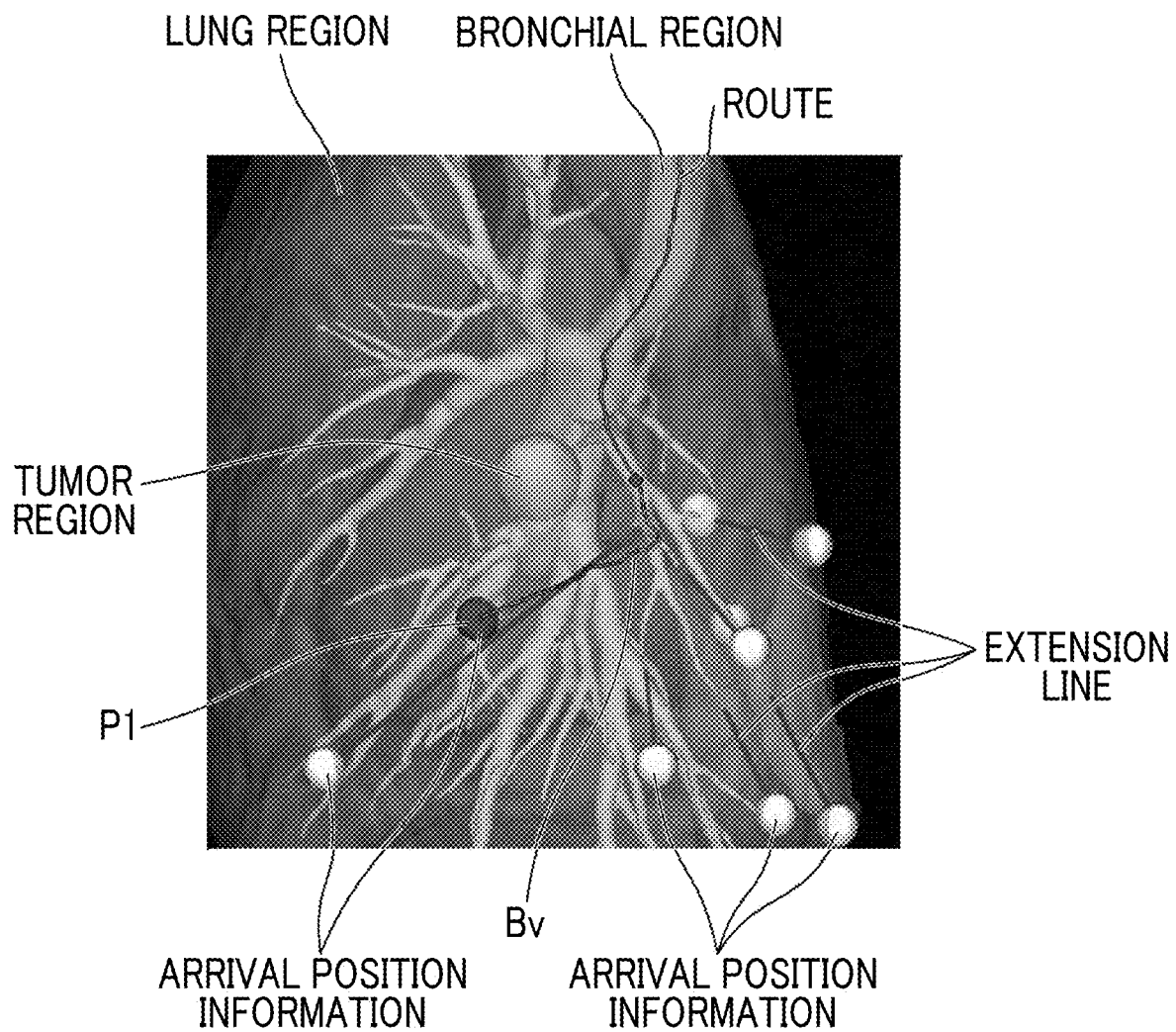
FIG. 3 is a diagram illustrating an example of a mapping image.

FIG. 3 is a diagram illustrating an example of the mapping image to be displayed on the display device 3. In the example of the mapping image illustrated in FIG. 3, the arrival position information is displayed as a sphere, and the extension line of the peripheral branch of the bronchial region is displayed as a bold line in gray. Further, the sphere at a center of the mapping image is an image indicating a tumor region. The arrival position information is estimated for all the peripheral branches and displayed on the mapping image, but it is assumed in FIG. 3 that only some of the pieces of arrival position information are illustrated, and a display of the other pieces of arrival position information is omitted.

In a state in which the mapping image including the arrival position information as illustrated in FIG. 3 is displayed, for example, in a case where the user selects the specific arrival position information P1 on the basis of a positional relationship with the tumor region, the display control unit 15 displays a route up to a peripheral branch Bv related to the arrival position information P1 as illustrated in FIG. 3, and displays the specific arrival position information P1 in a different color from the other arrival position information.

In this case, the arrival position information estimation unit 14 estimates the above-described assumed mapping information in a case where the branch By related to the arrival position information P1 selected by the user is set as a specific peripheral branch and the branch Br is set as a target branch, and outputs the assumed mapping information to the display control unit 15.

Figure 4:
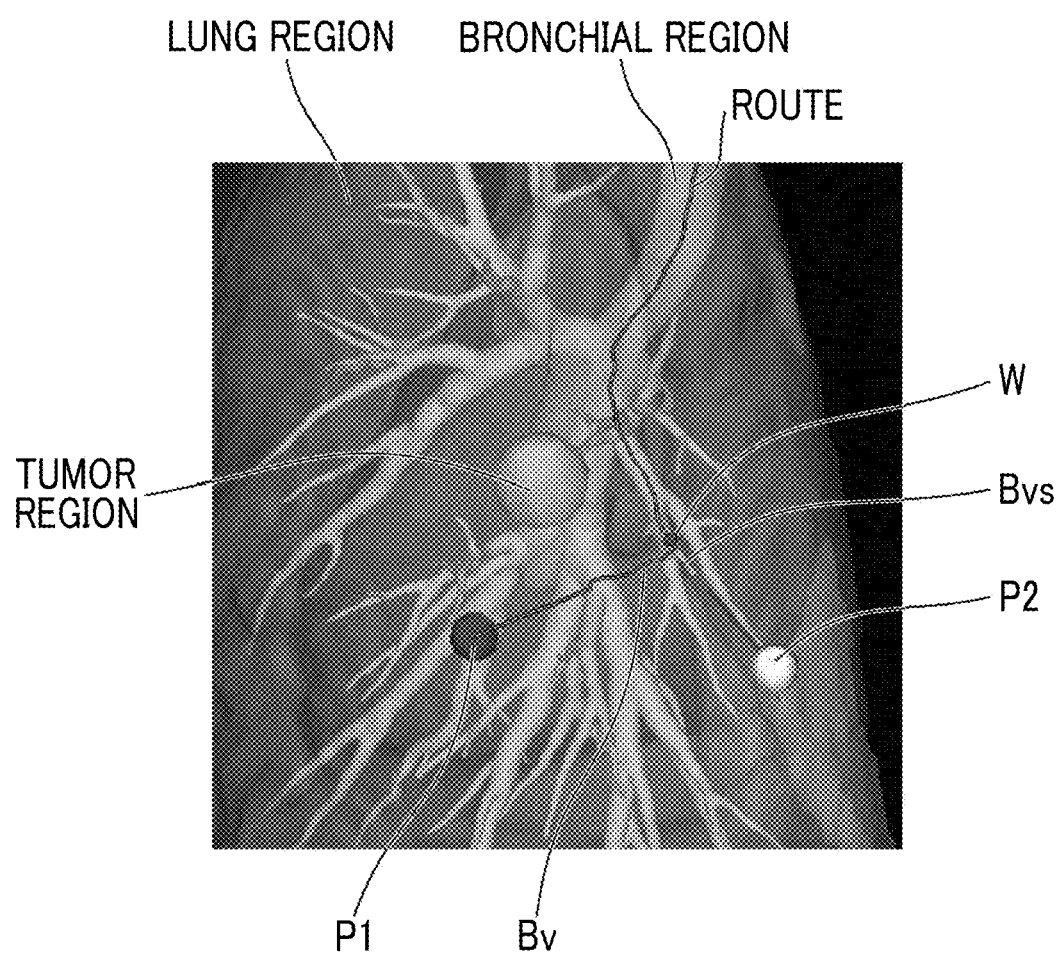
FIG. 4 is a diagram illustrating an example in which only arrival position information of a specific peripheral branch and assumed mapping information are displayed on a mapping image.

In a case where the assumed mapping information is input, the display control unit 15 generates and displays a mapping image obtained by superimposing only the arrival position information selected by the user and the arrival position information of the assumed mapping information on the volume rendering image. FIG. 4 is a diagram illustrating an example of the mapping image. FIG. 4 illustrates the mapping image in a case where the assumed mapping information is estimated using a first branch point W from the terminal of the branch By, and the arrival position information P2 of the peripheral branch Bvs extending from the branch point W is displayed as assumed mapping information on the mapping image. Further, FIG. 5 is a mapping image in a case where the assumed mapping information is estimated using a second branch point X from the terminal of the branch Bv, and arrival position information P2, P3, and P4 of peripheral branches Bvs, Bv3, and Bv4 extending from the branch point X are displayed as the assumed mapping information on the mapping image.

Figure 5:
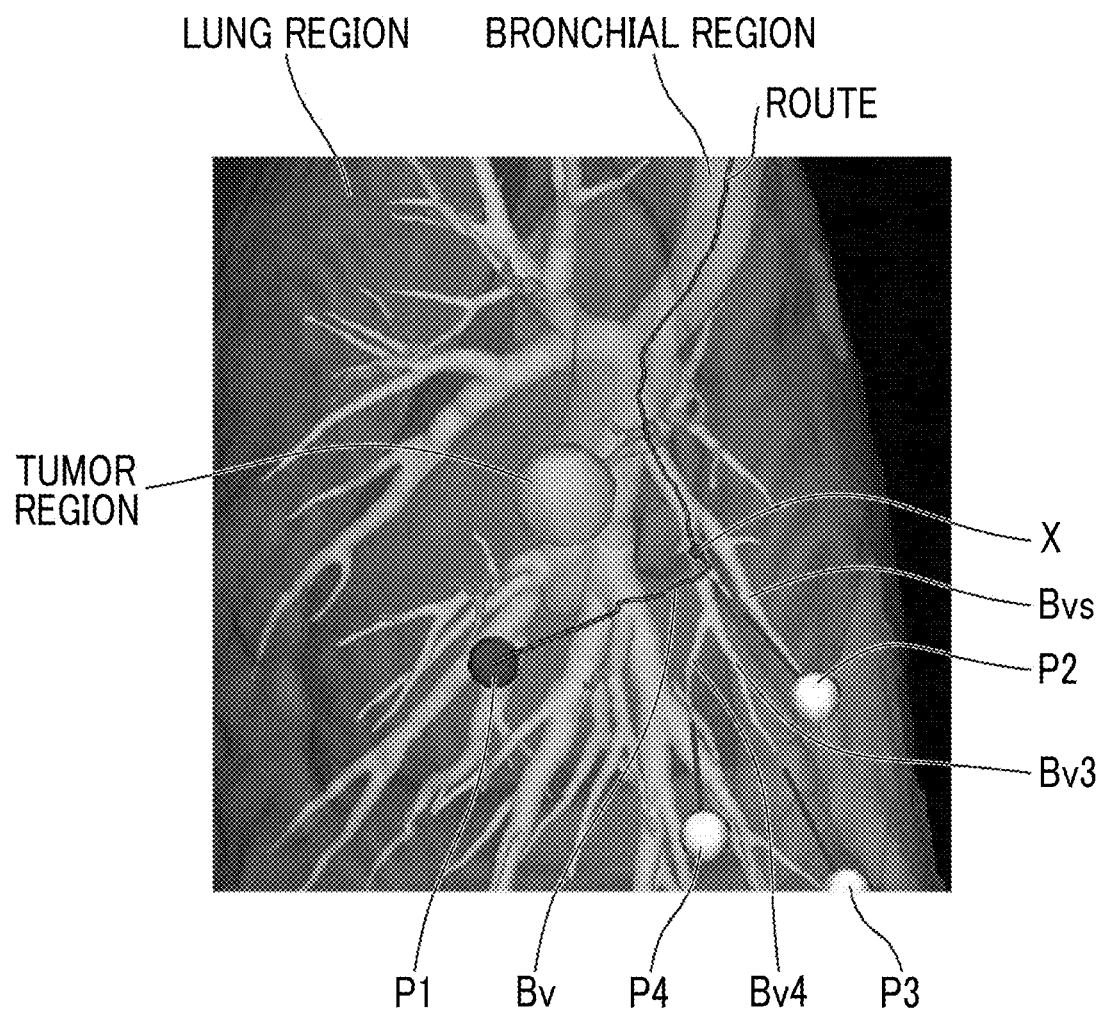
FIG. 5 is a diagram illustrating another example in which only arrival position information of a specific peripheral branch and assumed mapping information are displayed on a mapping image.

In the examples illustrated in FIGS. 4 and 5, only the arrival position information selected by the user and the arrival position information of the assumed mapping information are displayed on the mapping image, but the present invention is not limited thereto and other arrival position information may be displayed on the mapping image, and the arrival position information selected by the user and the arrival position information of the assumed mapping information may be displayed on the mapping image in a different display form from the other arrival position information. Specifically, the arrival position information selected by the user and the arrival position information of the assumed mapping information may be displayed in a different color or in a different shape from the other arrival position information.

Further, in the above description, the user selects the specific arrival position information in a case where the arrival position information of the assumed mapping information is displayed, but the present invention is not limited thereto. For example, the arrival position information may be automatically selected by specifying the arrival position information closest to the tumor region.

Further, a size of the sphere indicating the arrival position information displayed within the mapping image can be arbitrarily set by the user using the input device 4. Further, the sphere indicating the arrival position information may be switchable between a display and a non-display, or may be displayed to blink. Further, the extension line of the bronchial region does not have to be necessarily displayed, and may be switchable between a display and a non-display by the user.

The display device 3 includes a display device such as a liquid crystal display, and displays the above-described volume rendering image, and the like.

The input device 4 receives various setting inputs from the user, and includes an input device such as a keyboard and a mouse. The input device 4 receives, for example, a setting input of identification information of a patient, a setting input of opacity and color of the volume rendering image, a setting input of the display shape and the size of the arrival position information, and a selection of the specific arrival position information. The display device 3 and the input device 4 may be integrated by using a touch panel.

Figure 6:
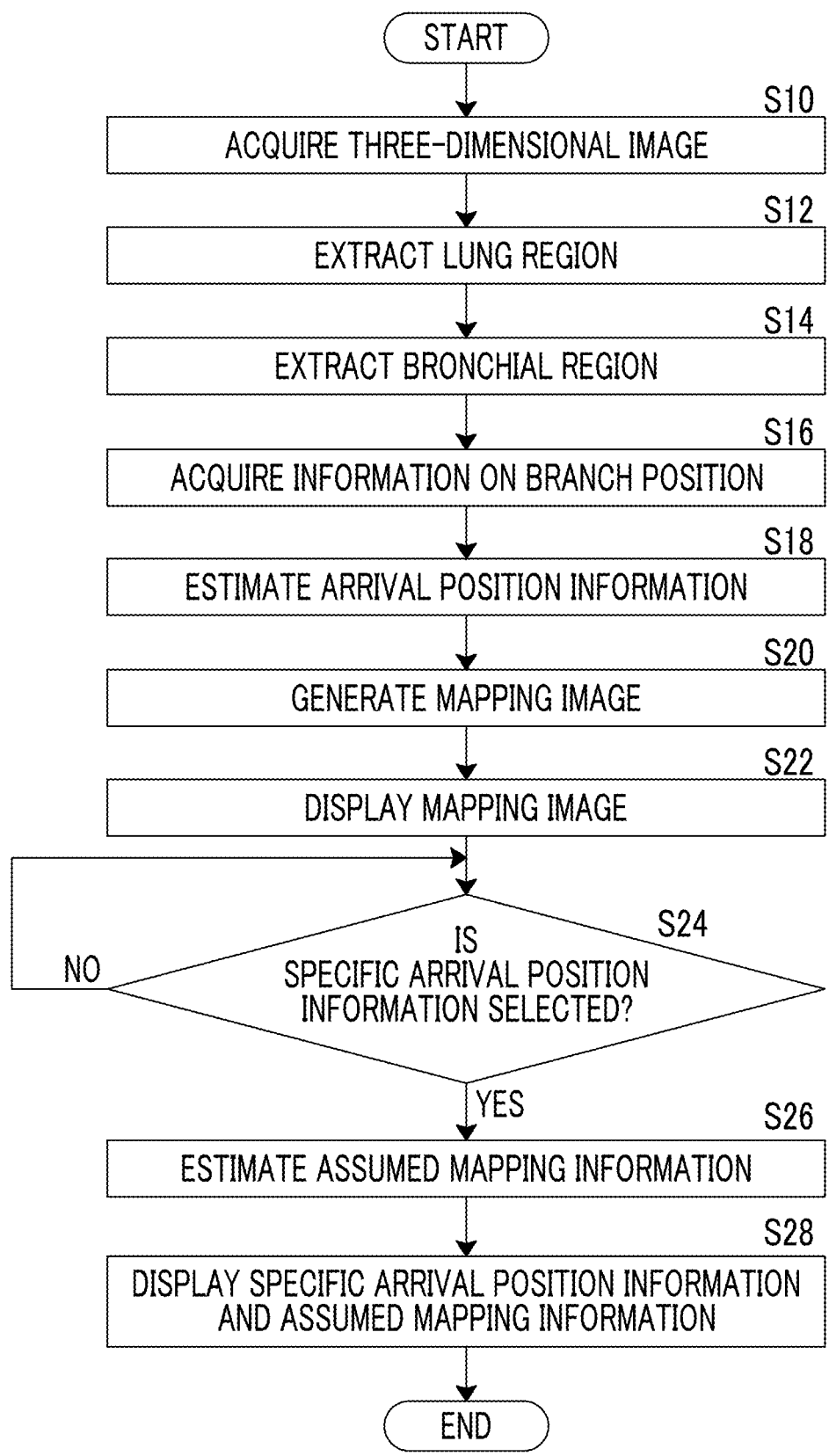
FIG. 6 is a flowchart illustrating an operation of a medical image diagnosis support system using an embodiment of the mapping image display control device, method, and program of the present invention.

Next, an operation of the medical image diagnosis support system of this embodiment will be described with reference to a flowchart illustrated in FIG. 6.

First, the medical image acquisition unit 10 reads and acquires the three-dimensional image 6 from the medical image storage server 2 on the basis of the input of the identification information of the patient from the user (S10).

The three-dimensional image 6 acquired by the medical image acquisition unit 10 is input to the lung region extraction unit 11 and the bronchial region extraction unit 12. The lung region extraction unit 11 extracts the lung region from the input three-dimensional image 6 (S12), and the bronchial region extraction unit 12 extracts the bronchial region from the input three-dimensional image 6 and acquires a graph structure in which the bronchial region is thinned (S14).

The graph structure acquired by the bronchial region extraction unit 12 is input to the branch position information acquisition unit 13. The branch position information acquisition unit 13 acquires information on the branch position of the bronchial region on the basis of the input graph structure (S16).

The information on the branch position acquired by the branch position information acquisition unit 13 is input to the arrival position information estimation unit 14. The arrival position information estimation unit 14 sets the extension line of the peripheral branch of the bronchial region on the basis of the input information on the branch position, and acquires information on an intersection between the extension line and the lung region surface as the arrival position information (S18).

The lung region extracted by the lung region extraction unit 11 and the bronchial region extracted by the bronchial region extraction unit 12 are input to the display control unit 15. The display control unit 15 generates the volume rendering image on the basis of the input lung region and the input bronchial region. Further, the extension line of the peripheral branch of the bronchial region set in the arrival position information estimation unit 14, and the arrival position information are input to the display control unit 15. The display control unit 15 generates mapping image obtained by superimposing the input extension line of the peripheral branch and the input arrival position information on the volume rendering image of the lung region and the bronchial region (S20), and displays the mapping image on the display device 3 (S22).

Then, in a case where the specific arrival position information is selected from among a plurality of pieces of arrival position information displayed on the mapping image (YES in S24), the arrival position information estimation unit 14 estimates the assumed mapping information in a case where the peripheral branch related to the arrival position information selected by the user is set as a specific peripheral branch and the branch is set as a target branch (S26), and outputs the assumed mapping information to the display control unit 15.

In a case where the assumed mapping information is input, the display control unit 15 generates and displays a mapping image obtained by superimposing only the arrival position information selected by the user and the arrival position information of the assumed mapping information on the volume rendering image (S28).

Next, a medical image diagnosis support system according to a second embodiment of the present invention will be described. A schematic configuration of the medical image diagnosis support system of the second embodiment is the same as that of the first embodiment illustrated in FIG. 1, but the assumed mapping information estimated by the arrival position information estimation unit 14 is different from the first embodiment. Therefore, the description will be given by focusing on the assumed mapping information herein.

In a case where a specific peripheral branch is set as a target branch and a bronchoscope is actually inserted toward the target branch as described above, the bronchus may be bent due to stiffness of the bronchoscope. In this case, a direction in which the peripheral branch of the bronchus extends is likely to be different from a direction of the extension line set in a case where the arrival position information is estimated.

Therefore, the arrival position information estimation unit 14 of the second embodiment assumes bending of the bronchus as described above in consideration of a load on the branch, estimates a direction in which the peripheral branch extends during surgery, and estimates the assumed mapping information on the basis of the estimated direction.

Conditions of deformation (bending) of the bronchus in a case where the bronchoscope is inserted may be set, for example, for each peripheral branch in the bronchial region in advance, or deformation conditions may be set for each branch position of the bronchial region, a branch position present between the terminal of the specific peripheral branch and the proximal end portion of the bronchus may be specified in a case where a specific peripheral branch is selected, and the assumed mapping information may be estimated on the basis of the deformation condition of the specified branch position.

Figure 7:
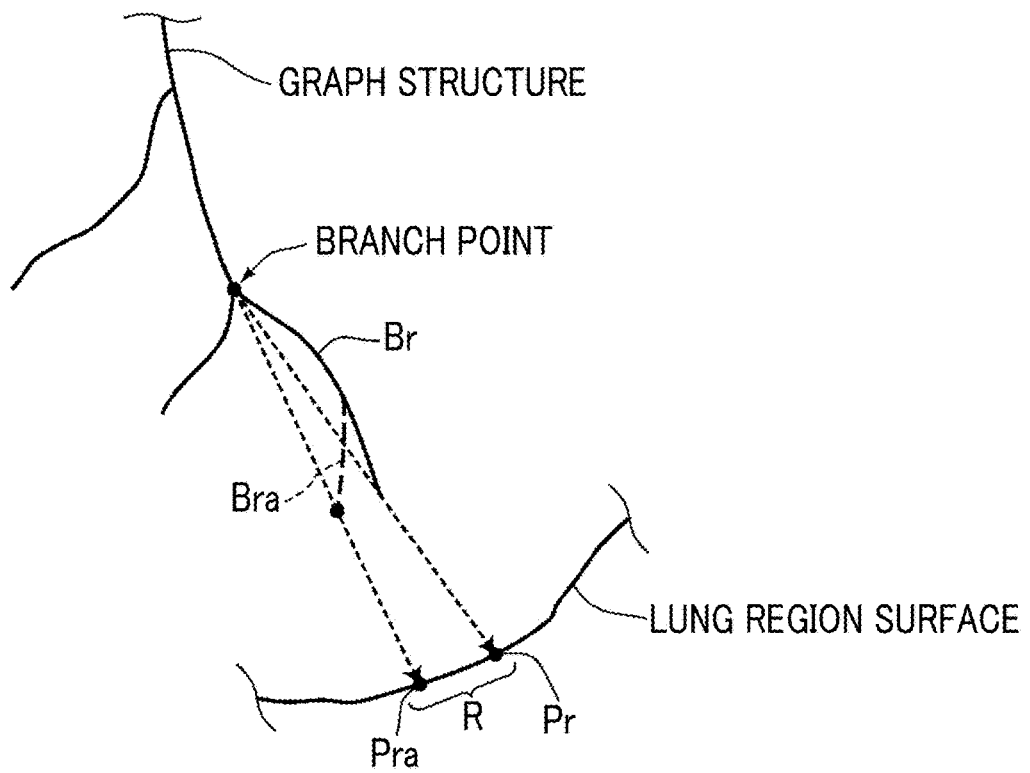
FIG. 7 is a diagram illustrating a method of estimating assumed mapping information in consideration of deformation of a bronchus.

Specifically, the arrival position information estimation unit 14 of the second embodiment estimates a branch Bra after deformation for a specific peripheral branch Br on the basis of its deformation condition, and estimates arrival position information Pra of the branch Bra, as illustrated in FIG. 7. A method of estimating the arrival position information Pra is the same as that in the first embodiment.

A region R on the lung region surface including both the arrival position information Pr of the specific peripheral branch Br and the arrival position information Pra of the branch Bra after deformation is estimated as the assumed mapping information. The region R may be a circle having a diameter that is a line segment connecting the arrival position information Pr to the arrival position information Pra, or may be a circle having a radius that is a line segment connecting the arrival position information Pr to the arrival position information Pra and having a center that is the arrival position information Pr. Further, the arrival position information Pra may be the assumed mapping information.

In a case where the arrival position information Pr illustrated in FIG. 7 is selected from among a plurality of pieces of arrival position information displayed on the mapping image, the arrival position information estimation unit 14 of the second embodiment estimates information on the region R or the arrival position information Pra described above as the assumed mapping information, and outputs the assumed mapping information to the display control unit 15.

The display control unit 15 generates and displays a mapping image obtained by superimposing the arrival position information Pr selected by the user, and an index indicating the region R and/or the arrival position information Pra on the volume rendering image.

According to the medical image diagnosis support system of the first and second embodiments, since the condition considering the erroneous insertion of the catheter or the deformation of the bronchus is preset and the assumed mapping information is estimated on the basis of the condition and displayed on the mapping image, the user can determine a resection region of a tumor or the like in consideration of a positional deviation in a case where a dye is actually sprayed onto the peripheral part of the bronchus.

Further, since a deviation of a staining position can be recognized in advance, it is not necessary to perform capturing of a CT image for confirming the staining position after staining treatment.

In the first embodiment, the region may be set on the basis of the arrival position information of the specific peripheral branch and the assumed mapping information, and the mapping image obtained by superimposing the index indicating the region on the volume rendering image may be generated and displayed, similar to the second embodiment.

Further, in a case where the assumed mapping information is estimated, arrival position information different from the arrival position information of the specific peripheral branch may be estimated in consideration of the erroneous insertion of the catheter as in the first embodiment and in consideration of the deformation of the bronchus as in the second embodiment, and accordingly, the assumed mapping information may be estimated.

Figure 8:
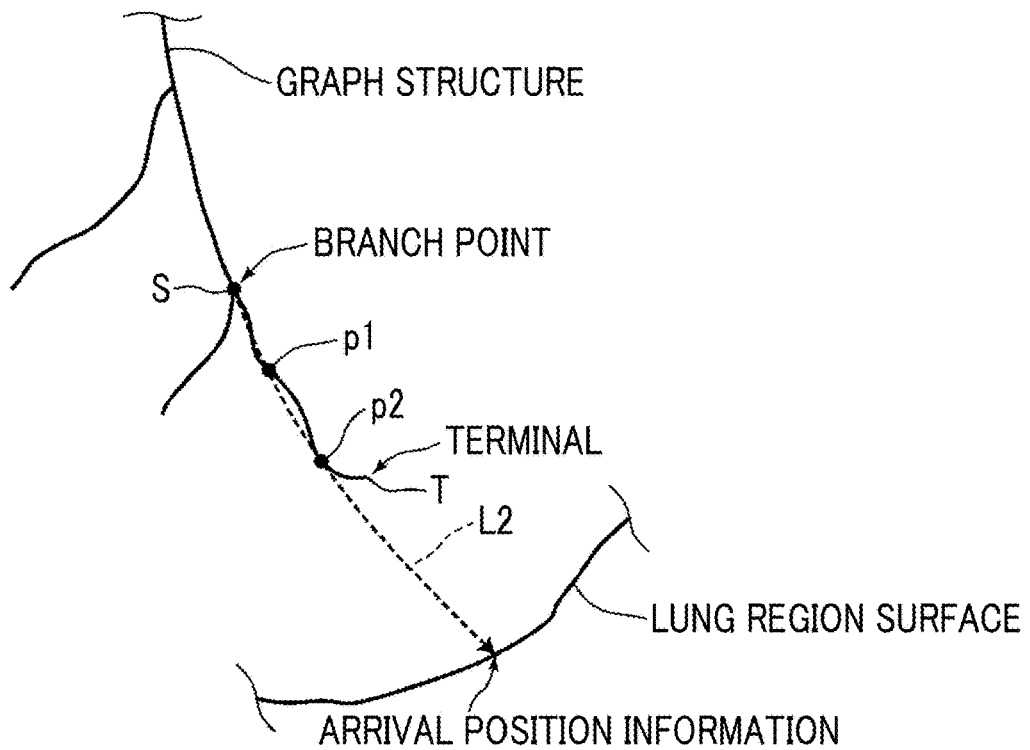
FIG. 8 is a diagram illustrating a case where a curve subjected to spline interpolation using two points on a peripheral branch and a branch point is estimated as an extension line of a peripheral branch of a bronchial region.

Further, in the first and second embodiments, the straight line connecting the terminal to the branch point in the graph structure is estimated as the extension line of the peripheral branch of the bronchial region, but a method of setting the extension line of the peripheral branch of the bronchial region is not limited thereto. For example, as illustrated in FIG. 8, spline interpolation may be performed using two points p1 and p2 on the peripheral branch and a first branch point S from the terminal T of the peripheral branch, and a curve L2 obtained by the spline interpolation may be estimated as the extension line of the peripheral branch.

In a case where the curve L2 obtained by the spline interpolation is estimated as the extension line of the peripheral branch, it is possible to estimate the extension line of the peripheral branch with higher accuracy.

Even in the case in which the extension line of the peripheral branch is estimated by the spline interpolation as described above, the branch point S may not be necessarily used or a point near the branch point S may be used so long as substantially the same result can be obtained.

Figure 9:
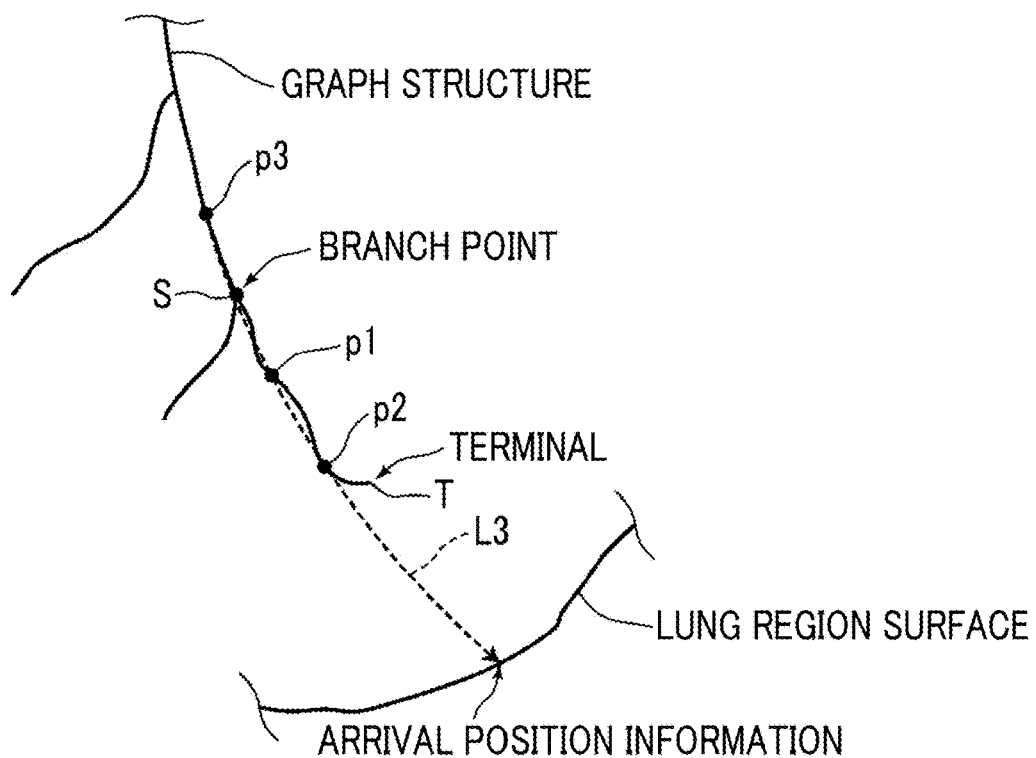
FIG. 9 is a diagram illustrating another example in a case where an extension line of the peripheral branch of the bronchial region is estimated by spline interpolation.

Further, although the spline interpolation is performed using the branch point S and the two points p1 and p2 on the peripheral branch in the above description, three or more points are set for points other than the branch point S. Further, the spline interpolation may be performed using at least one of point p1, the branch point S, or a point p3 on the peripheral branch on the trachea upstream side of the branch point S to estimate a curve L3, as illustrated in FIG. 9, instead of setting the two points on the peripheral branch as illustrated in FIG. 8. It is desirable for the point p3 to be set between the branch point S and an immediately previous branch point toward the trachea upstream side from the branch point S. The points p1 to p3 used for the spline interpolation may be arbitrarily set by the user using the input device 4 or distances from the branch point S may be set in advance and the points may be automatically set.

Further, the peripheral branch may be specified on the basis of the information on the branch position acquired by the branch position information acquisition unit 13, a dominant region of the specified peripheral branch in the lung region may be specified, and a straight line connecting a center of gravity of the dominant region to the terminal of the peripheral branch may be estimated as the extension line of the peripheral branch of the bronchial region.

Figure 10:
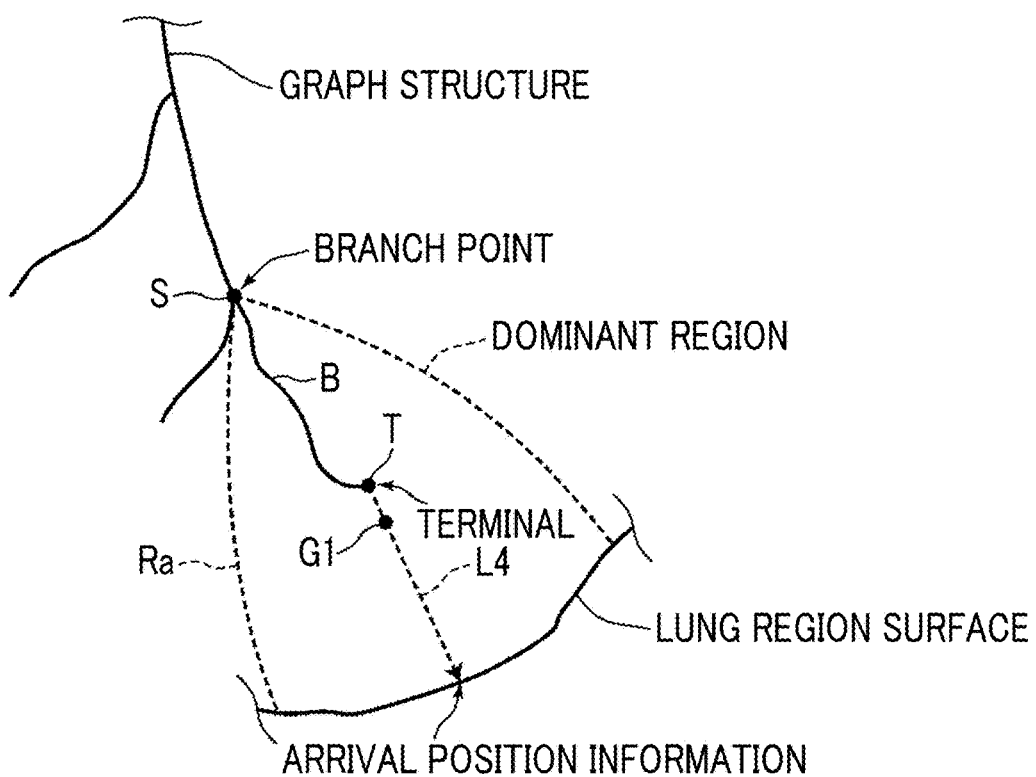
FIG. 10 is a diagram illustrating a case where a straight line connecting a center of gravity of a dominant region of a peripheral branch to a terminal of the peripheral branch is estimated as the extension line of the peripheral branch of the bronchial region.

Specifically, as illustrated in FIG. 10, a peripheral branch B may be specified on the basis of the branch point S acquired by the branch position information acquisition unit 13, a dominant region Ra of the peripheral branch B in the lung region may be specified, and a straight line L4 connecting a center of gravity G1 of the dominant region Ra to a terminal T of the peripheral branch B may be estimated as the extension line of the peripheral branch of the bronchial region. The dominant region Ra of the peripheral branch of the bronchial region is preset for each peripheral branch from the anatomical point of view, and the center of gravity G1 referred to herein is a center of gravity in the three-dimensional space of the dominant region having a three-dimensional shape.

Thus, in a case where the straight line L4 connecting the center of gravity G1 of the dominant region Ra to the terminal T of the peripheral branch B is estimated as the extension line of the peripheral branch B of the bronchial region, it is possible to estimate the extension line of the peripheral branch with higher accuracy on the basis of the anatomical point of view.

Further, as another method of estimating the arrival position on the lung surface of the extension line of the peripheral branch using the dominant region of the peripheral branch of the bronchial region as described above, for example, the peripheral branch may be specified on the basis of the information on the branch position acquired by the branch position information acquisition unit 13, the dominant region of the specified peripheral branch in the lung region may be specified, and a center of gravity of a region that is a surface of the lung region in a surface of the dominant region may be estimated as the arrival position information.

Figure 11:
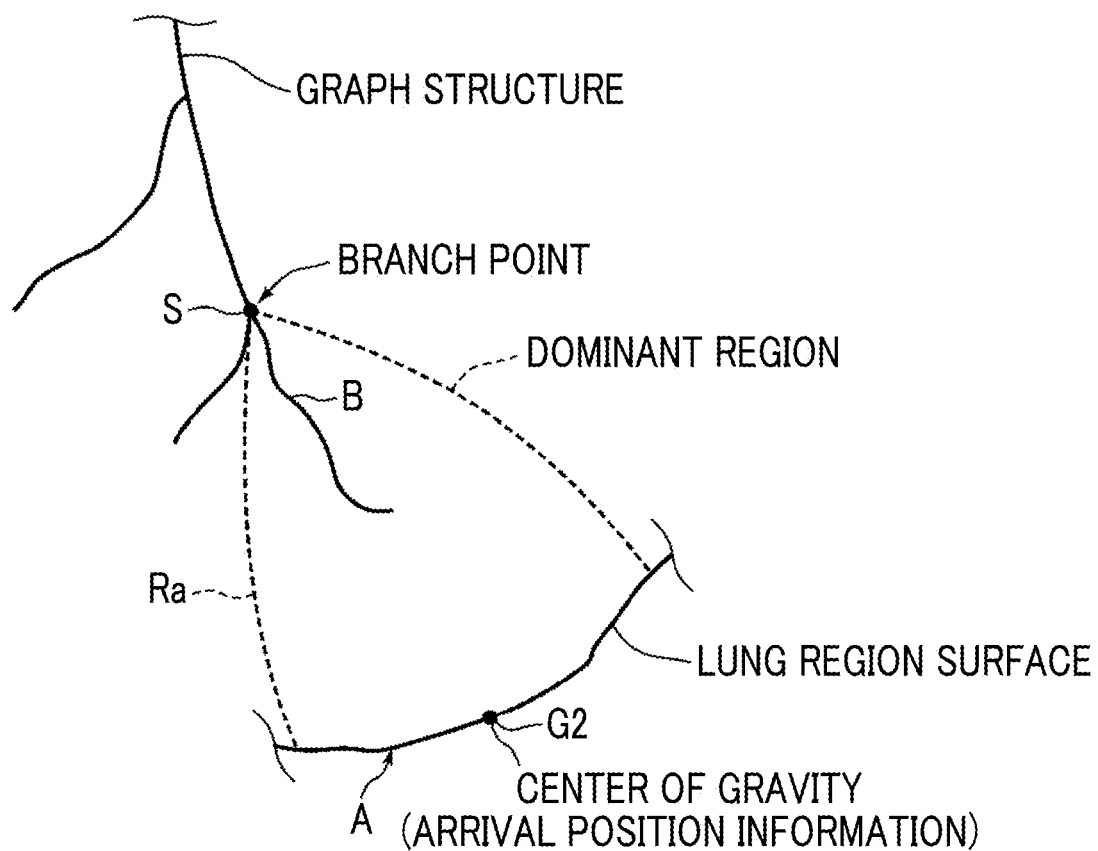
FIG. 11 is a diagram illustrating a case where a center of gravity of a region that is a surface of a lung region in a surface of a dominant region is estimated as arrival position information.

Specifically, as illustrated in FIG. 11, a peripheral branch B may be specified on the basis of the branch position S acquired by the branch position information acquisition unit 13, a dominant region Ra of the peripheral branch B in the lung region may be specified, and a center of gravity G2 of a region A that is a surface of the lung region in a surface of the dominant region Ra may be estimated as the arrival position information. The center of gravity G2 referred to herein is a center of gravity of the region A represented as a surface in a three-dimensional space.

Further, it is known that there are a pulmonary artery and a pulmonary vein around the bronchus, and an extension direction of the bronchus is similar to an extension direction of the pulmonary artery and the pulmonary vein. Therefore, a position at which the extension line of the peripheral branch of the bronchial region arrives at the lung surface may be estimated on the basis of information on the pulmonary artery or the extension direction of the pulmonary artery.

Figure 12:
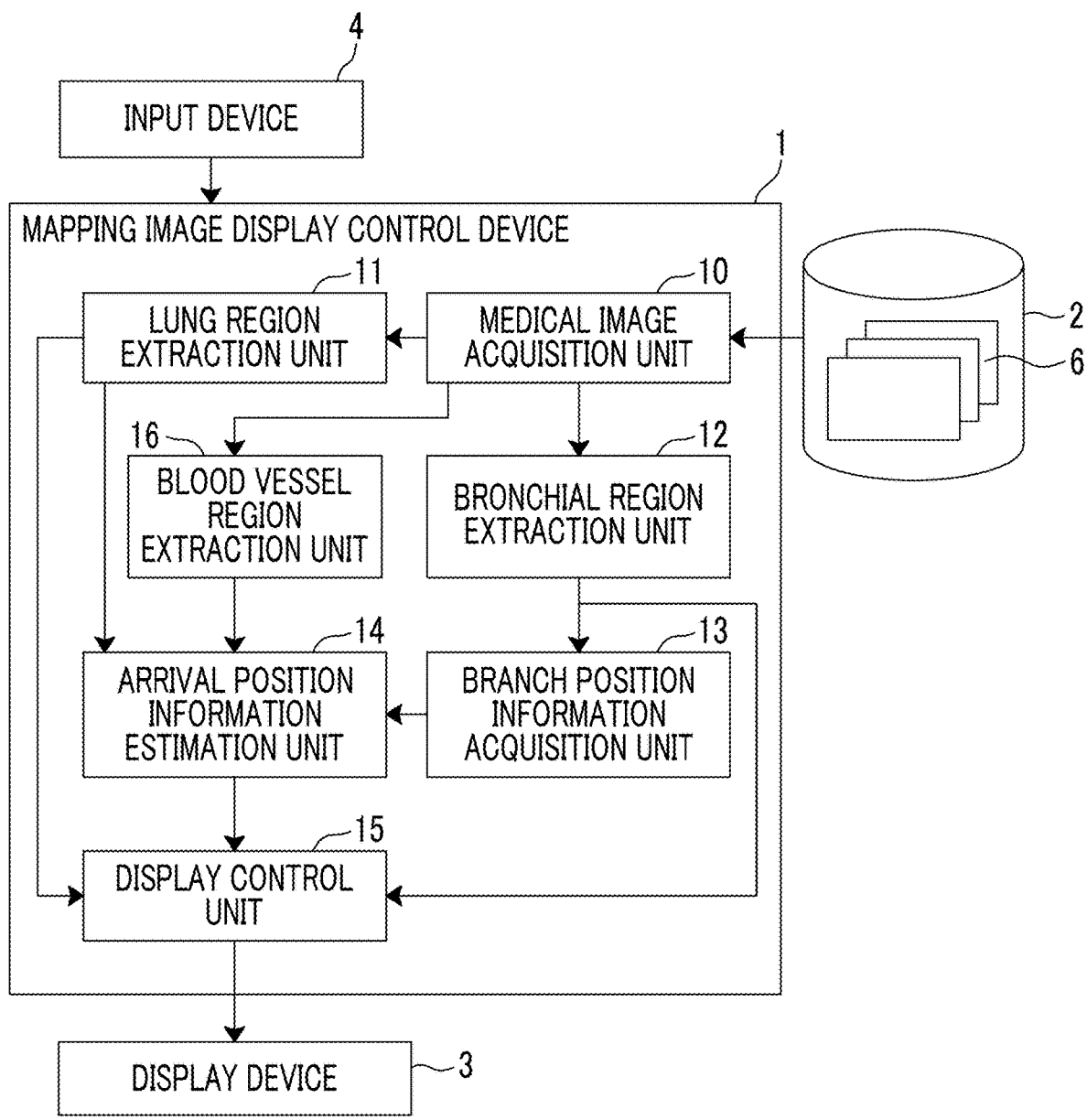
FIG. 12 is a block diagram illustrating a schematic configuration of a medical image diagnosis support system further including a blood vessel region extraction unit.

Specifically, as illustrated in FIG. 12, a blood vessel region extraction unit 16 is further provided for the mapping image display control device 1. The blood vessel region extraction unit 16 extracts a blood vessel region included in the lung region from the three-dimensional image 6. Specifically, the blood vessel region extraction unit 16 extracts a pulmonary artery region and a pulmonary vein region. For example, a known method such as a region spreading method can be used as a method of extracting the pulmonary artery region and the pulmonary vein region.

Figure 13:
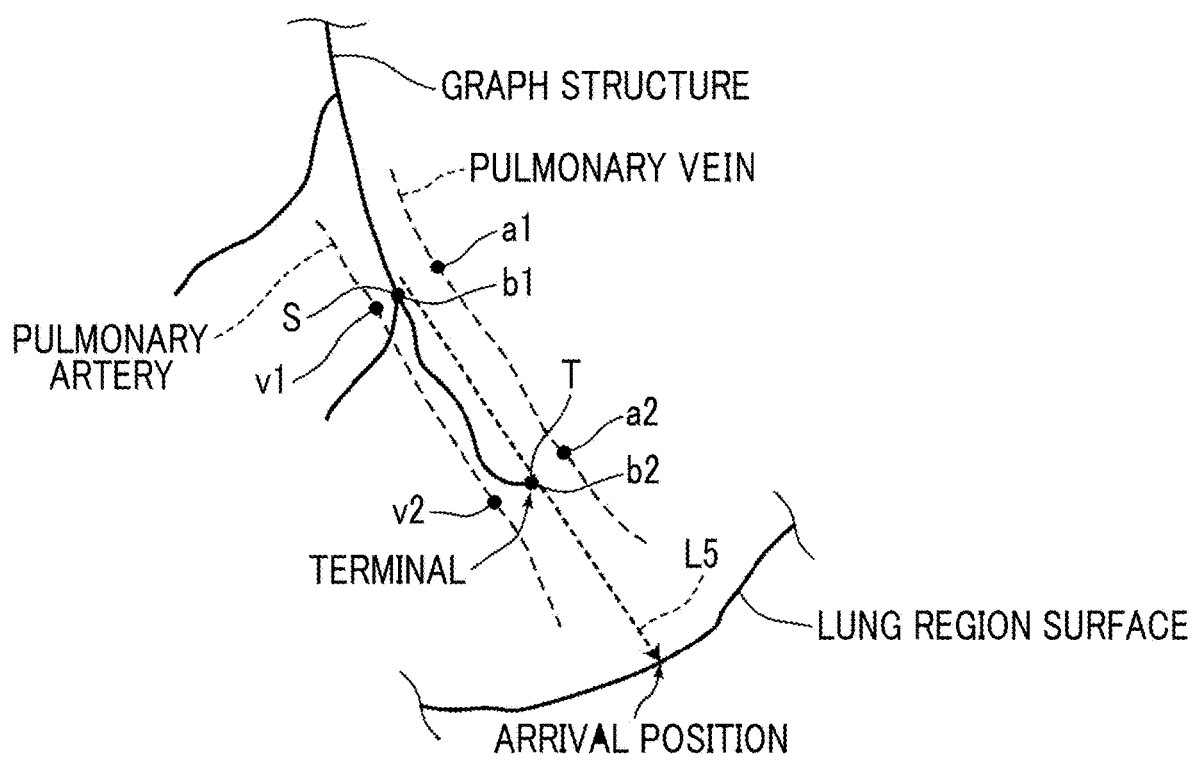
FIG. 13 is a diagram illustrating a case where a position at which an extension line of a peripheral branch of a bronchial region arrives at a lung surface is estimated on the basis of information on a blood vessel region and a branch position.

The arrival position information estimation unit 14 specifies the pulmonary artery region and the pulmonary vein region extending along the peripheral branch of the bronchial region on the basis of the information on the branch position acquired by the branch position information acquisition unit 13, and estimates the extension line of the peripheral branch of the bronchial region on the basis of the pulmonary artery region and the pulmonary vein region. Specifically, as illustrated in FIG. 13, the arrival position information estimation unit 14 detects a position v1 of the pulmonary artery region closest to the branch point S acquired by the branch position information acquisition unit 13 and a position a1 of the pulmonary vein region closest to the branch point S, and detects a position v2 in the pulmonary artery region closest to the terminal T of the peripheral branch of the graph structure and a position a2 in the pulmonary vein region closest to the terminal T.

The branch point S is the first branch point b1 from the terminal T of the peripheral branch of the graph structure to the trachea upstream side. Further, the position v1 in the pulmonary artery region closest to the branch point S (b1) is a position in the pulmonary artery region of which the distance to the branch point S is the shortest, and the position a1 in the pulmonary vein region closest to the branch point S is a position in the pulmonary vein region of which the distance to the branch point S is the shortest. Further, the position v2 in the pulmonary artery region closest to the terminal T (b2) is a position in the pulmonary artery region of which the distance to the terminal T is the shortest, and the position a2 in the pulmonary vein region closest to the terminal T is a position in the pulmonary vein region of which the distance to the terminal T is the shortest.

A direction from the position v1 to the position v2 in the pulmonary artery region is estimated as the extension direction of the pulmonary artery region to set a first vector, a direction from the position a1 to the position a2 in the pulmonary vein region is estimated as the extension direction of the pulmonary vein region to set the second vector, and an average of the first vector and the second vector is calculated. A straight line L5 obtained by extending such an average vector is estimated as the extension line of the peripheral branch of the bronchial region, and a position at which this extension line arrives at the lung surface is acquired.

By estimating the extension line of the peripheral branch using the pulmonary vein region and the pulmonary artery region as described above, it is possible to estimate the extension line of the peripheral branch with higher accuracy on the basis of the anatomical point of view.

Although the first vector is set using the position v1 and the position v2 in the pulmonary artery region and the second vector is set using the position a1 and the position a2 in the pulmonary vein region in the above description, for example, spline interpolation may be performed to set a first curve using the position v1 and the position v2 in the pulmonary artery region and a point between these positions, the spline interpolation may be performed to set a second curve using the position a1 and the position a2 in the pulmonary vein region and a point between these positions, and a curve obtained by averaging the first curve and the second curve may be estimated as the extension line of the peripheral branch of the bronchial region.

Further, although the extension line of the peripheral branch is estimated using both of the pulmonary vein region and the pulmonary artery region in the above description, the extension line of the peripheral branch may be estimated using only one of the pulmonary vein region and the pulmonary artery region. For example, a straight line that is parallel to the first vector set on the basis of the pulmonary artery region and passes through the terminal T of the peripheral branch may be estimated as the extension line of the peripheral branch. Further, a straight line that is parallel to the second vector set on the basis of the pulmonary vein region and passes through the terminal T of the peripheral branch may be estimated as the extension line of the peripheral branch.

What is claimed is:

1. A mapping image display control device comprising:
a processor configured to:
extract a lung region included in a three-dimensional image;
extract a bronchial region included in the lung region;
acquire information on a branch position of the bronchial region;
estimate arrival position information at which an extension line of a specific peripheral branch included in the bronchial region as a target branch arrives at a surface of the lung region on a basis of the information on the branch position;
set a condition of an erroneous insertion of a catheter inserting into a bronchus erroneously;
estimate, on the basis of the condition of the erroneous insertion, assumed mapping information at which an extension line of another peripheral branch that is erroneously inserted with the catheter arrives at the surface of the lung region, the another peripheral branch being different from the specific peripheral branch and the another peripheral branch extending from a branch position that is present between a proximal end portion of the bronchial region and the specific peripheral branch, and the arrival position information and the assumed mapping information representing a point or a range at which a dye arrives when the dye is sprayed from within the bronchial region toward the specific peripheral branch; and
generate a mapping image obtained by mapping the arrival position information of the specific peripheral branch and the assumed mapping information to the surface of the lung region and display the mapping image on a display.

2. The mapping image display control device according to claim 1, wherein the another peripheral branch extends from a first branch position or a second branch position from a terminal of the specific peripheral branch.

3. The mapping image display control device according to claim 1, wherein the processor is further configured to estimate a straight line set on the basis of the information on the branch position and the specific peripheral branch as the extension line of the branch.

4. The mapping image display control device according to claim 3, wherein the processor is further configured to estimate a straight line set on the basis of a terminal of the specific peripheral branch and information on a first branch position from the terminal as the extension line of the specific peripheral branch.

5. The mapping image display control device according to claim 1, wherein the processor is further configured to perform spline interpolation using a point on the specific peripheral branch and a point specified on the basis of the information on the first branch position from the terminal of the specific peripheral branch, and estimate a curve obtained by the spline interpolation as the extension line of the specific peripheral branch.

6. The mapping image display control device according to claim 1, wherein the processor is further configured to specify the specific peripheral branch on the basis of the information on the branch position, specify a dominant region of the specific peripheral branch in the lung region, and estimate a straight line connecting a center of gravity of the dominant region to a terminal of the specific peripheral branch as the extension line of the specific peripheral branch.

7. The mapping image display control device according to claim 1, wherein the processor is further configured to specify the specific peripheral branch on the basis of the information on the branch position, specify a dominant region of the specific peripheral branch in the lung region, and estimate a center of gravity of a region that is a surface of the lung region in a surface of the dominant region as the arrival position information.

8. The mapping image display control device according to claim 1,
wherein the processor is further configured to extract a blood vessel region included in the lung region, and estimate the extension line of the specific peripheral branch on the basis of information on the blood vessel region and the branch position.

9. The mapping image display control device according to claim 8, wherein the processor is further configured to extract at least one of a pulmonary vein region or a pulmonary artery region as the blood vessel region.

10. The mapping image display control device according to claim 1, wherein the processor is further configured to set a region on the basis of the arrival position information of the specific peripheral branch and the assumed mapping information, generate a mapping image obtained by mapping the region on the surface of the lung region, and display the mapping image on the display.

11. A mapping image display control method comprising:
extracting a lung region included in a three-dimensional image;
extracting a bronchial region included in the lung region;
acquiring information on a branch position of the bronchial region;
estimating arrival position information at which an extension line of a specific peripheral branch included in the bronchial region as a target branch arrives at a surface of the lung region on a basis of the information on the branch position;
setting a condition of an erroneous insertion of a catheter inserting into a bronchus erroneously;
estimating, on the basis of the condition of the erroneous insertion, assumed mapping information at which an extension line of another peripheral branch that is erroneously inserted with the catheter arrives at the surface of the lung region, the another peripheral branch being different from the specific peripheral branch and the arrival position information and the assumed mapping information representing a point or a range at which a dye arrives when the dye is sprayed from within the bronchial region toward the specific peripheral branch; and
generating a mapping image obtained by mapping the arrival position information of the specific peripheral branch and the assumed mapping information to the surface of the lung region and displaying the mapping image on a display.

12. A non-transitory computer-readable storage medium storing therein a mapping image display control program that causes a computer to implement the method of claim 11.

13. A mapping image display control device, comprising:
a processor configured to:
extract a lung region included in a three-dimensional image;
extract a bronchial region included in the lung region;
acquire information on a branch position of the bronchial region;
estimate arrival position information at which an extension line of a specific peripheral branch included in the bronchial region as a target branch arrives at a surface of the lung region on a basis of the information on the branch position;
set a condition of a bronchus deformation of the bronchus in a case where a bronchoscope is inserted into the bronchus;
estimate assumed mapping information at which an extension line of a deformed peripheral branch in which the specific peripheral branch is deformed according to the condition of the bronchus deformation arrives at the surface of the lung region, the arrival position information and the assumed mapping information representing a point or a range at which a dye arrives when the dye is sprayed from within the bronchial region toward the specific peripheral branch; and
generate a mapping image obtained by mapping the arrival position information of the specific peripheral branch and the assumed mapping information to the surface of the lung region and display the mapping image on a display,
wherein the bronchus deformation is determined based on deformation conditions of branch positions between a terminal of the specific peripheral branch and the proximal end portion of the bronchus, the deformation conditions being set for the respective branch position of the bronchial region in advance of the bronchoscope being inserted into a patient.

14. A mapping image display control method comprising:
extracting a lung region included in a three-dimensional image;
extracting a bronchial region included in the lung region;
acquiring information on a branch position of the bronchial region;
estimating arrival position information at which an extension line of a specific peripheral branch included in the bronchial region as a target branch arrives at a surface of the lung region on a basis of the information on the branch position;
setting a condition of a bronchus deformation of the bronchus in a case where a bronchoscope is inserted into the bronchus;
estimating assumed mapping information at which an extension line of a deformed peripheral branch in which the specific peripheral branch is deformed according to the condition of the bronchus deformation arrives at the surface of the lung region, the arrival position information and the assumed mapping information representing a point or a range at which a dye arrives when the dye is sprayed from within the bronchial region toward the specific peripheral branch; and
generating a mapping image obtained by mapping the arrival position information of the specific peripheral branch and the assumed mapping information to the surface of the lung region and display the mapping image on a display,
wherein the bronchus deformation is determined based on deformation conditions of branch positions between a terminal of the specific peripheral branch and the proximal end portion of the bronchus, the deformation conditions being set for the respective branch position of the bronchial region in advance of the bronchoscope being inserted into a patient.

15. A non-transitory computer-readable storage medium storing therein a mapping image display control program that causes a computer to implement the method of claim 14.

* * * * *